(12) United States Patent
Bal et al.

(10) Patent No.: US 9,579,213 B2
(45) Date of Patent: Feb. 28, 2017

(54) INTERVERTEBRAL EXPANDABLE CAGE SYSTEM AND ITS INSTRUMENT

(71) Applicant: Kamil Bal, Ankara (TR)

(72) Inventors: Kamil Bal, Ankara (TR); Ibrahim Ozgur Bektas, Ankara (TR)

( * ) Notice: Subject to any disclaimer, the term of this patent is extended or adjusted under 35 U.S.C. 154(b) by 0 days.

(21) Appl. No.: 14/650,269

(22) PCT Filed: Dec. 6, 2013

(86) PCT No.: PCT/TR2013/000359
§ 371 (c)(1),
(2) Date: Jun. 5, 2015

(87) PCT Pub. No.: WO2014/088521
PCT Pub. Date: Jun. 12, 2014

(65) Prior Publication Data
US 2015/0305881 A1    Oct. 29, 2015

(30) Foreign Application Priority Data

Dec. 6, 2012   (TR) .............................. TR2012/14213

(51) Int. Cl.
*A61F 2/44* (2006.01)
*A61F 2/46* (2006.01)
(Continued)

(52) U.S. Cl.
CPC .............. *A61F 2/442* (2013.01); *A61F 2/447* (2013.01); *A61F 2/4611* (2013.01);
(Continued)

(58) Field of Classification Search
CPC ...... A61F 2/4455; A61F 2/446; A61F 2/4465; A61F 2/447; A61F 2002/4475; A61F 2/44
See application file for complete search history.

(56) References Cited

U.S. PATENT DOCUMENTS 5,554,191 A * 9/1996 Lahille ............... A61B 17/1757
411/55
5,653,763 A * 8/1997 Errico ..................... A61F 2/446
411/55

(Continued)

FOREIGN PATENT DOCUMENTS

DE       4323956 C1      10/1994
DE       10113689 C1      8/2002

(Continued)

OTHER PUBLICATIONS

Translation to English of FR 2815845 A1; accessed from epo.org on Nov. 16, 2015.*

(Continued)

*Primary Examiner* — Eduardo C Robert
*Assistant Examiner* — Julianna N Harvey
(74) *Attorney, Agent, or Firm* — Venjuris PC

(57) ABSTRACT

An expandable cage (1) for maintaining a distance between two vertebras on a spine and providing fusion is disclosed. The expandable cage (1) comprises a horizontal axis, a front part with an upper arm (1.1), a lower arm (1.2), and shaft fixation sockets (1.7.1 and 1.7.2) located between the arms (1.1 and 1.2), and a hollow shaft (2) with graft holes (2.4). The shaft (2) is placed parallel to the horizontal axis and partially inside the shaft fixation sockets (1.7.1 and 1.7.2). The cage (1) is expanded vertically by rotating the shaft (2) 90 degrees with an instrument, thus further separating vertically the upper arm (1.1) and the lower arm (1.2).

5 Claims, 5 Drawing Sheets

Figure 1:
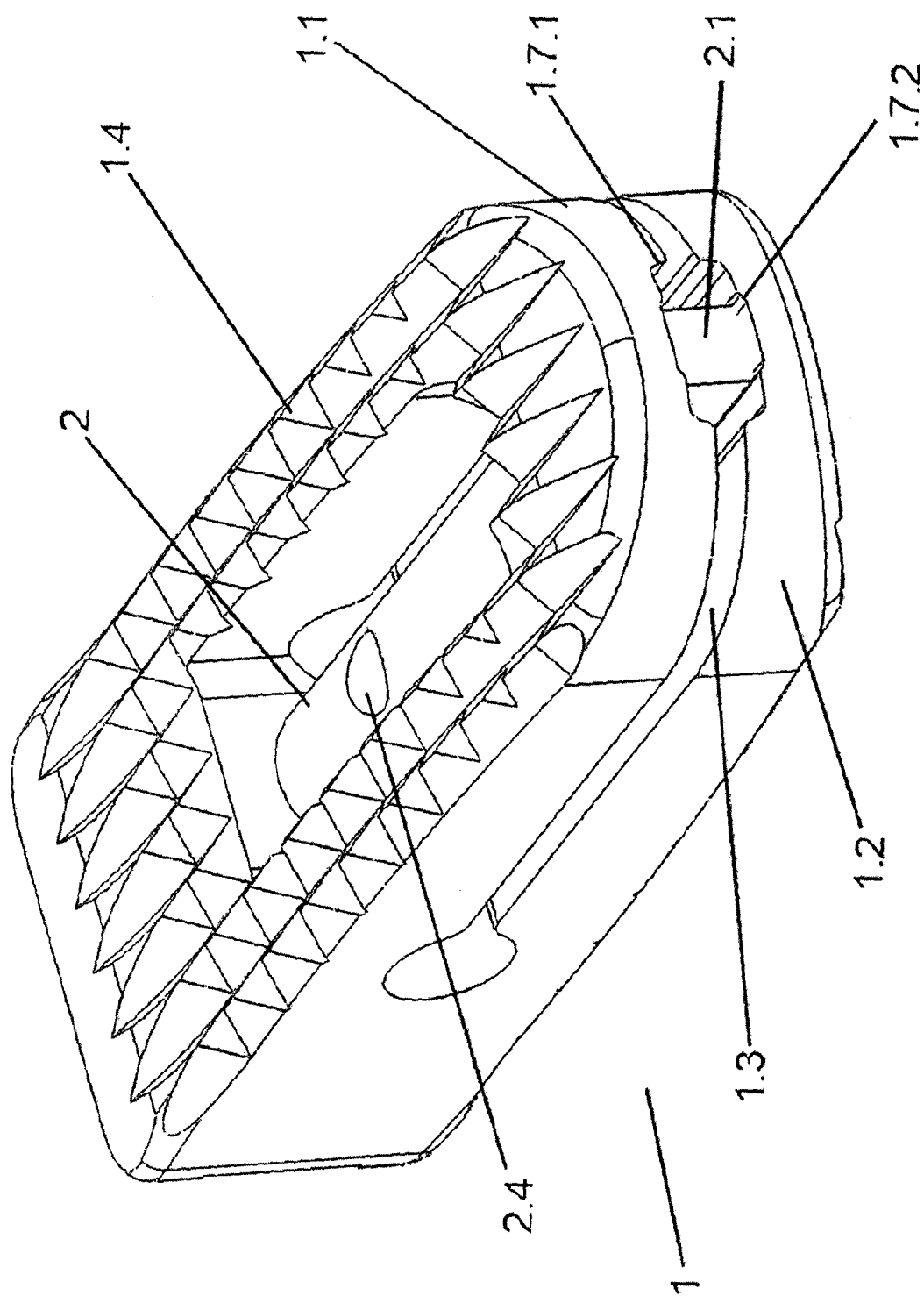

(51) Int. Cl.
*A61F 2/30* (2006.01)
*A61F 2/28* (2006.01)

(52) U.S. Cl.
CPC ... *A61F 2/30744* (2013.01); *A61F 2002/2835* (2013.01); *A61F 2002/3038* (2013.01); *A61F 2002/3082* (2013.01); *A61F 2002/30364* (2013.01); *A61F 2002/30365* (2013.01); *A61F 2002/30482* (2013.01); *A61F 2002/30484* (2013.01); *A61F 2002/30522* (2013.01); *A61F 2002/30538* (2013.01); *A61F 2002/30556* (2013.01); *A61F 2002/30596* (2013.01); *A61F 2002/30774* (2013.01); *A61F 2002/30843* (2013.01); *A61F 2002/30892* (2013.01); *A61F 2002/4475* (2013.01); *A61F 2002/4627* (2013.01); *A61F 2002/4629* (2013.01); *A61F 2230/0073* (2013.01); *A61F 2310/00017* (2013.01); *A61F 2310/00023* (2013.01); *A61F 2310/00161* (2013.01); *A61F 2310/00179* (2013.01)

(56) References Cited

U.S. PATENT DOCUMENTS

| | | | |
|---|---|---|---|
| 6,371,989 B1 | 4/2002 | Chauvin et al. | |
| 6,375,683 B1* | 4/2002 | Crozet | B65D 5/48022 623/17.15 |
| 7,220,280 B2 | 5/2007 | Kast et al. | |
| 2002/0045943 A1* | 4/2002 | Uk | A61F 2/446 623/17.16 |
| 2002/0068976 A1 | 6/2002 | Jackson | |
| 2002/0161444 A1 | 10/2002 | Choi | |
| 2002/0177897 A1* | 11/2002 | Michelson | A61F 2/44 623/17.11 |
| 2003/0208275 A1* | 11/2003 | Michelson | A61F 2/4455 623/17.16 |
| 2006/0206207 A1 | 9/2006 | Dryer et al. | |
| 2009/0208905 A1 | 8/2009 | Vachtenberg | |
| 2010/0049324 A1* | 2/2010 | Valdevit | A61F 2/447 623/17.16 |
| 2010/0057208 A1 | 3/2010 | Dryer et al. | |
| 2010/0286780 A1 | 11/2010 | Dryer et al. | |
| 2012/0029637 A1* | 2/2012 | Ragab | A61F 2/447 623/17.11 |
| 2012/0109319 A1 | 5/2012 | Perisic | |
| 2012/0271422 A1* | 10/2012 | Miller | A61F 2/447 623/17.16 |
| 2013/0108983 A1 | 5/2013 | Vachtenberg | |
| 2014/0094917 A1* | 4/2014 | Salerni | A61F 2/447 623/17.16 |

FOREIGN PATENT DOCUMENTS

| | | | |
|---|---|---|---|
| DE | 102005033608 A1 | 1/2007 | |
| EP | 0664994 A1 | 8/1995 | |
| EP | 1382315 A1 | 1/2004 | |
| EP | 1504735 A2 | 2/2005 | |
| FR | 2803741 A1 | 7/2001 | |
| FR | 2813519 A1 | 3/2002 | |
| FR | 2815845 A1 * | 5/2002 | ............ A61F 2/446 |
| FR | 2866228 A1 | 8/2005 | |
| TR | 200605027 A2 | 4/2008 | |
| WO | 2006078972 A2 | 7/2006 | |
| WO | 2008029215 A2 | 3/2008 | |
| WO | 2011007240 A1 | 1/2011 | |

OTHER PUBLICATIONS

International Search Report of WO2014088521A3 (PCT/TR2013/000359).

* cited by examiner

INTERVERTEBRAL EXPANDABLE CAGE SYSTEM AND ITS INSTRUMENT

TECHNICAL FIELD

The invention relates to an expandable cage system and a specific instrument to this cage, which is developed in the treatment of diseases on thoracic and lumbar spine and especially to maintain the distance between two vertebras on the spine and achieve fusion.

STATE OF ART

Human spine is formed by connection of different-sized bone structures called vertebra. Spine is along the back and supports the body. The spine protects the spinal cord which is one of the most important parts of neural system, thus prevents damages to it. Although the spine has a strong bone structure, it has elasticity at the same time which enables adjustment to the body movements.

The cause of this elasticity is the intervertebral disks between vertebras. These disks are fibrous cartilage structures that are soft in the center and more solid in the outer parts. The main function of the disks is to give dynamic structure to the vertebra and to protect it against shocks.

One or couple of these disks can be damaged because of diseases, aging, accidents etc. In case of this, the movement capability of the vertebra can decrease. Additionally, the nerve roots passing through inside of the spine can be damaged or compressed. In such situation, at the organ that specific nerve is related to (i.e. arms or legs); a loss of strength and sensation or chronic back and/or lower back pains can be encountered.

Many surgical techniques and methods were developed in the treatment of spinal vertebra diseases (fracture, kyphosis, degenerative disk disease, lordosis, and spondylolisthesis).

Out of these techniques, the most commonly known is to remove the disk between vertebras and implant intervertebral devices (ALIF, TLIF, ACIF, and PLIF) in place of it to maintain the distance between vertebras and speed up the fusion. The main purpose of these devices is to create the necessary environment for the ossification, to protect the distance between vertebra, to minimize the pressure on the nerves and to ensure non-deformation of the normal spinal curve until the fusion is achieved.

Since early 1900s, filling the place between two vertebras with another material is a known technique used in the treatment of intervertebral diseases. At the beginning, bone particles (autogenous-bone) taken from the patient's other bones (hip bone etc.) were used for this purpose. Suitably-long bone part or parts taken from the patient himself/herself were placed between vertebras to treat the disease. At the beginning of 1980s, stainless steel cages were invented by George Bagby. These cages were tested on animals first (especially on horses). Since 1989, cages manufactured from titanium alloy were used in clinical studies on humans. Using titanium cages were approved by American Food and Drug Administration (FDA) in 1996. Since then, several cages-intended to be used at neck (cervical) and back—lower back (thoraco-lumbar) spine—with different shapes (cylindrical, flat etc) and made of different materials (stainless steel, titanium alloy, PEEK-heretherketone, ceramic, carbon alloy etc) were manufactured and in use for more than 15 years.

In order to implant such cages between the vertebras, the distance between the two vertebras should be opened and the cage should be implanted through this opening. The screw systems and/or instruments are used for this opening process. Excessive opening of the distance between the vertebras can result in implantation of unsuitably sized (bigger) cages, damage to the nerves and deformation of natural structure of the spine.

As a solution to these problems, the expandable cage systems have been developed in the recent years. These cages can be implanted into their places without the need of a bigger opening between the vertebras, as the initial height of these cages is shorter than that of normal cage systems. Then, with the help of a mechanism, the height of the cages can be increased while they are in between the two vertebras. Hence, both a development in surgery technique and improvement in the health of the patient are achieved.

The general characteristics of these cages are; they should be in suitable size to fit the operated area, should have load-bearing walls and should have a mechanism which enables expanding the height of the cage after it is implanted between the vertebras.

Application TR200605027 and U.S. Pat. No. 6,371,989 are first examples to this type cages. These cylindrically shaped cages have four arms. A component that goes in between these arms enables the expansion of the arms and sets the cage into final position.

The problems that arise in the use of these cages is that due to their shapes, in some cases, it is problematic for them to stay firmly between the vertebras and during the surgery it is difficult to determine the expansion distance as the expansion distance is not fixed. The normal curve of the spine can be deformed, if the expansion distance is too low or too high.

Application U.S. Pat. No. 7,220,280 and DE102005033608 can also be given as an example to this type of cages. These cages have a rectangular prism shape and have two or four arms. A separate component that slides through these arms enables the expansion of the arms.

The problems that arise in the use of these cages are that, in some cases it is difficult to move the sliding separate component within the cage. The separate component may move backwards in case that there is no strong stopping mechanism which will put an end to the advance movement of the separate component. Additionally, as can be seen in the example of Application DE102005033608, when the separate component is slid forward more than the limit and in a strong manner, there is a probability that it can slide through and be released from the cage arms.

The expandable cages offer a more advanced treatment and several advantages to both the patient and the surgeon. But, their shapes and expansion mechanisms are the most important factors that affect the efficiency of the cages. The distance between the vertebras cannot be restored due to improper use of these cages and result in further damage both to the vertebras where the cage is implanted and to the adjacent vertebras.

AIM OF THE INVENTION

An aim of the invention starting from the current status of the technique is: to eliminate the existing defects with the help of improvements made in cage systems, which achieves fusion and maintains the distance between two vertebras in spine surgery operations, and its specific instrument.

Another aim of this invention is to expand the height of the intervertebral cage by turning the dynamic shaft—which is placed into the cage in parallel with the cage—by 90 degrees and to achieve firm implantation of the cage into the place between the vertebras.

Another aim of this invention is that, the dynamic shaft within the cage has a hollow shape with holes on it. In this way, after the cage is implanted between the vertebra, in order to speed up the fusion, bone graft can be injected into the shaft and with the help of the holes, this bone graft can reach to the interior parts of the cage.

Another aim of this invention is that, with the help of an instrument specifically designed for this cage, the cage can easily be implanted between the vertebras and after implantation, with the help of the shaft adapter on the instrument—without the need for another instrument—the shaft can be turned 90 degrees and the cage is enabled to reach the expansion position.

DESCRIPTION OF FIGURES AND REFERENCE NUMBERS

In order to explain the invention better, drawings—which is detailed below—are attached:
1. General overview of the expandable cage system
2. Back view of the expandable cage system
3. General overview of the shaft
4. General overview of the instrument
5. General overview of the of the disassembled instrument Parts of the Figures are numbered as follows:
1. Expandable Cage
    1.1 Expandable cage upper arm
    1.2 Expandable cage lower arm
    1.3 Expandable cage cut
    1.4 Lower and upper teeth
    1.5 Instrument hollow
    1.6 Threaded instrument hole
    1.7 Shaft fixation socket
        1.7.1 Outer socket
        1.7.2 Inner socket
    1.8 Central space
2. Shaft
    2.1 Frontal expansion end
    2.2 Cornered back end
    2.3 Shaft body
    2.4 Graft holes
    2.5 Graft filling hole
3. Instrument
    3.1 Handle
    3.2 Shaft Adapter
        3.2.1 Shaft adapter end
        3.2.2 Shaft adapter handle
    3.3 Cage Fixator
        3.3.1 Outer cage fixator
            3.3.1.1 Cage fixator claw
        3.3.2 Inner cage fixator
            3.3.2.1 Cage fixator threads
            3.3.2.2 Inner cage turning fixator
            3.3.2.3 Shaft adapter handle stopper.

DETAILED DESCRIPTION OF THE INVENTION

The intervertebral expandable cage system and its instrument which is the scope of this invention, comprise of in general terms; an intervertebral expandable cage (1), a shaft (2) which is placed into the expandable cage (1) in parallel with expandable cage (1) axis and an instrument (3) which enables the system to be implanted between the vertebras.

Figure 2:
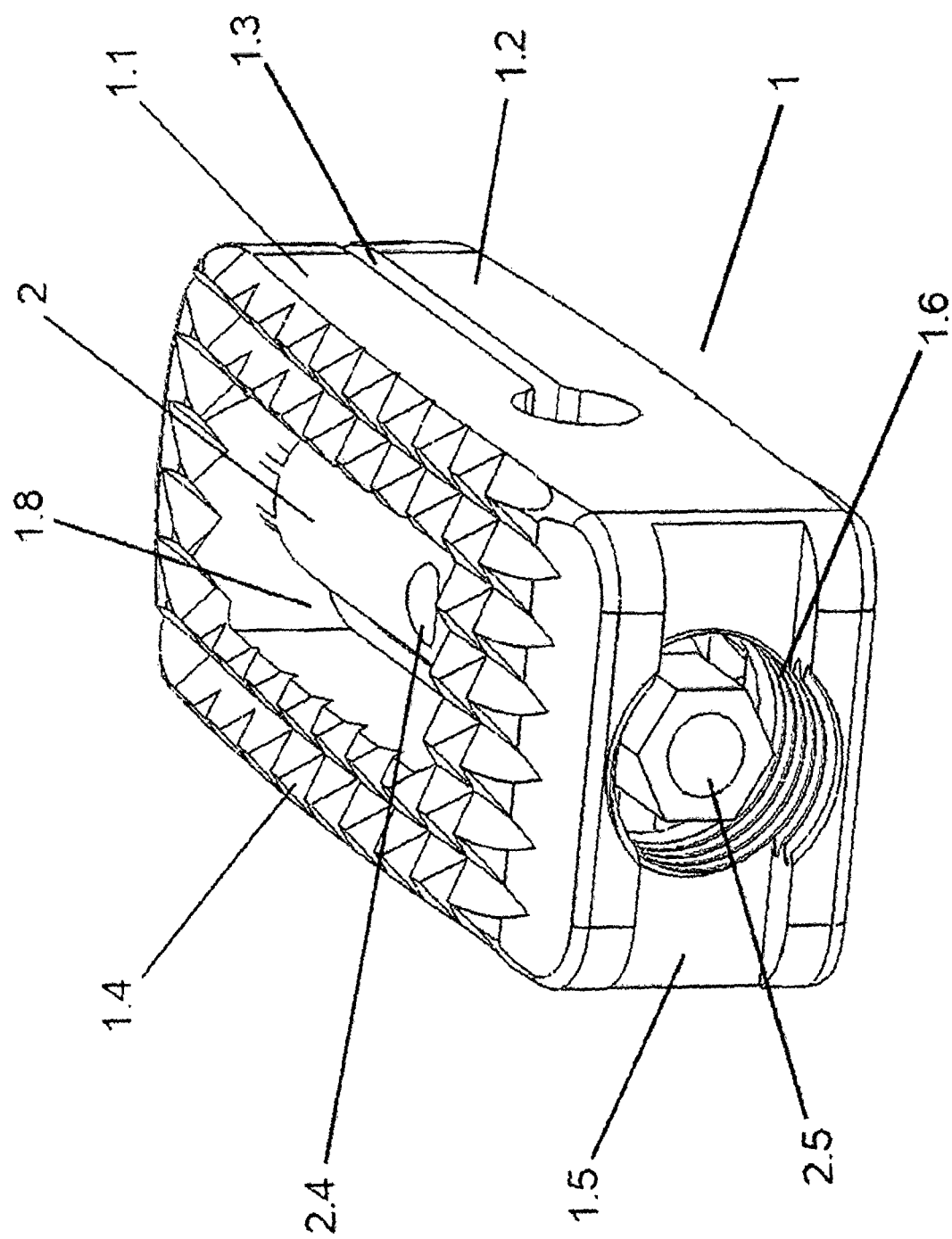

The expandable cage (1) shown in detail in FIG. 1-2 comprises of; an expandable cage upper arm (1.1) which enables the cage (1) to be expandable, an expandable cage lower arm (1.2), an expandable cage cut (1.3), lower and upper teeth (1.4) which enables firm hold of the cage (1) into the vertebras, an instrument hollow (1.5) and a threaded instrument hole (1.6) and an outer socket (1.7.1) which the frontal expansion end (2.1) of the shaft (2) will fit into in closed position and an inner socket (1.7.2) which the frontal expansion end (2.1) of the shaft (2) will fit into and fixed in open position and a central space (1.8) which is suitable for bone graft filling in case of a need.

The cage (1) is preferable made of PEEK (polyetheretherketone) material. However it can be made of from stainless steel, titanium, titanium alloy, carbon, ceramic or a material that is bio compatible and strong enough to prevent damaging of the structure.

There are lower and upper teeth (1.4) on the lower and upper surfaces of the cage (1) that are in parallel to the cage (1) horizontal axis. These upper and lower teeth (1.4), after the cage (1) is implanted between the vertebras, enable it to be firmly situated and prevent the cage (1) to move backwards especially.

At the back of the expandable cage (1), there is an instrument hollow (1.5), which enables cage fixator threads (3.3.2.1) at the end of the instrument (3) to be fixed to the cage (1) and a threaded instrument hole (1.6) which the shaft adapter end (3.2.1) at the end of the instrument (3) goes into. Instrument hole (1.6) can be in a threaded form or can have a cavity, tab, teeth or thread which will allow the inner cage fixator (3.2.2) to grasp the end of it. As an advantage, instrument hollow (1.5) and threaded instrument hole (1.6) are placed in such a way that they enable using a single instrument (3) which can perform all processes.

As an advantage, there are shaft fixation sockets (1.7) on the expandable cage upper arm (1.1) and expandable cage lower arm (1.2) which are placed at the front of the expandable cage (1). When the shaft (2) is turned to open position, that is when the cage is expanded, the frontal expansion end (2.1) of the shaft (2) sits in the inner socket (1.7.2) and system fixation is achieved. In the pre-cage expansion position, frontal expansion end (2.1) sits in the outer socket (1.7.1) in a fixed position. With the turning movement applied by the instrument (3) to the shaft (2), the frontal expansion end (2.1) of the shaft (2) slides from outer socket (1.7.1) to the inner socket (1.7.2) and provides a secure locking and expansion with the help of the effective fixation. Thanks to the sliding claw structure in the shaft fixation sockets (1.7), a clear information as to the completion of the locking is provided to the surgeon.

Figure 3:
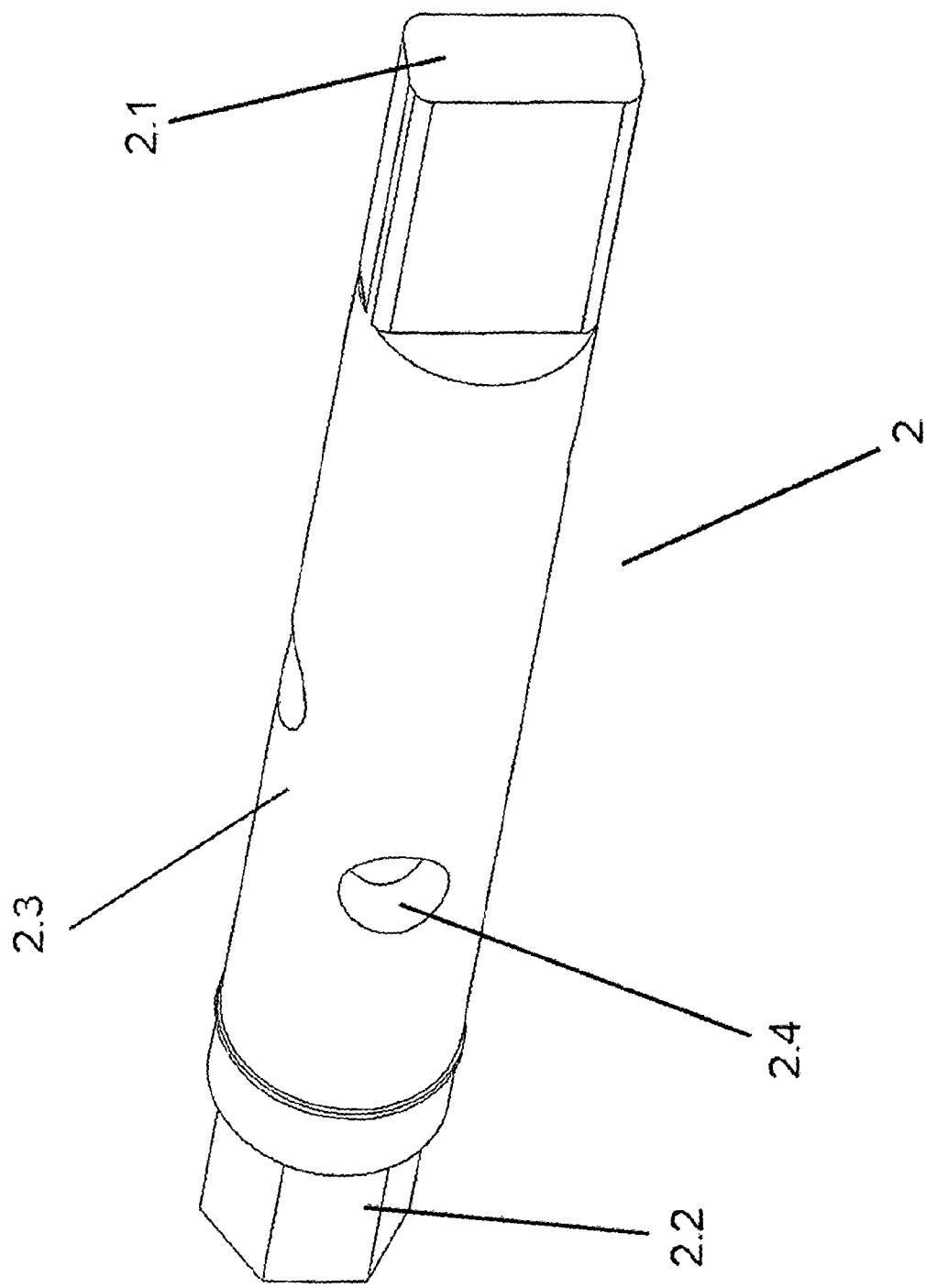

The shaft (2) as shown in detail in FIG. 3; comprises of frontal expansion end (2.1), cornered back end (2.2), shaft body (2.3), graft holes (2.4) and graft filling hole (2.5).

The shaft (2) is preferable made of titanium alloy material. However it can be made of from stainless steel, PEEK (polyetheretherketone), titanium, carbon, ceramic or a material that is bio compatible and strong enough to prevent damaging of the structure.

Preferably and as an advantage, the cornered back end (2.2) of the shaft (2) has a hexagonal form which enables a suitable instrument to grip it and turn the shaft (2) in the desired direction and angle. It is also possible that the back end of the shaft (2.2) can be in different cornered geometrical forms or state of the art structures which enable the instrument (3) to grip it. Thus, due to the hexagonal back end of the shaft (2.2), during surgery, the shaft (2) can firmly be turned, until the expandable cage upper arm (1.1) and expandable cage lower arm (1.2) are expanded in proper angle between the vertebras and frontal expansion end (2.1) of the shaft (2) sits on the inner socket (1.7.2) at the front of the expandable cage (1).

As an advantage, the shaft (2) is located in the middle of the cage (1). Due to this, during surgery, it is possible to place bone grafts to speed up the fusion process into the central space (1.8) in the middle of the expandable cage (1). As an advantage, due to round shape of the body (2.3) of the shaft (2) and keeping its initial volume during the movement, the expansion movement does not affect the structure of the bone grafts.

As an advantage, the shaft (2) has a hollow interior and there are graft holes (2.4) on it. After the expandable cage (1) is implanted into its place between the vertebras, during the surgery, with the help of the graft filling hole (2.5) at the back of the shaft (2), a suitable bone graft can be injected into the shaft (2). The bone graft which is injected through graft filling hole (2.5) fills into the central space (1.8) in the middle of the expandable cage (1) with the help of graft holes (2.4) on the shaft (2).

Figure 4:
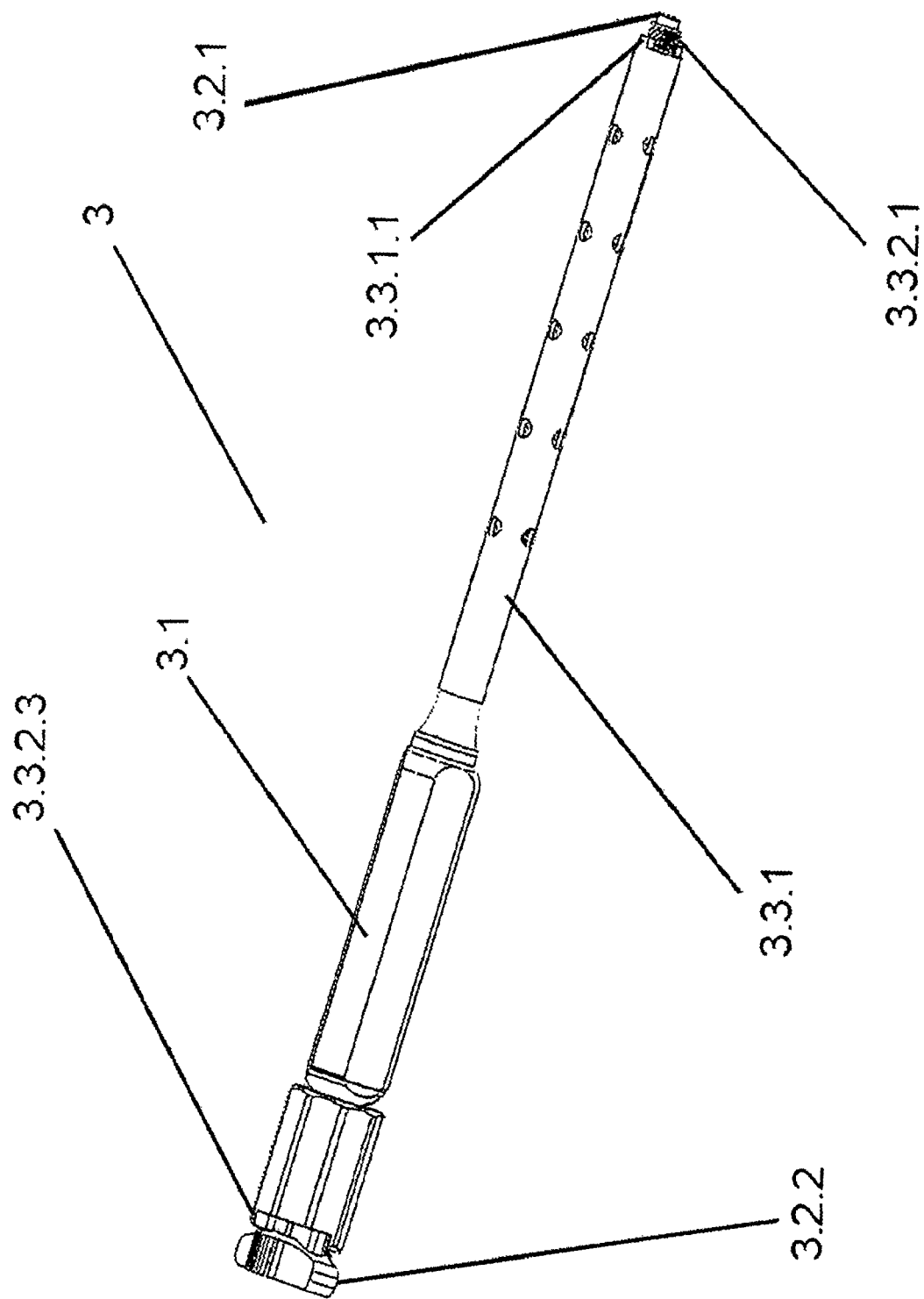
Figure 5:
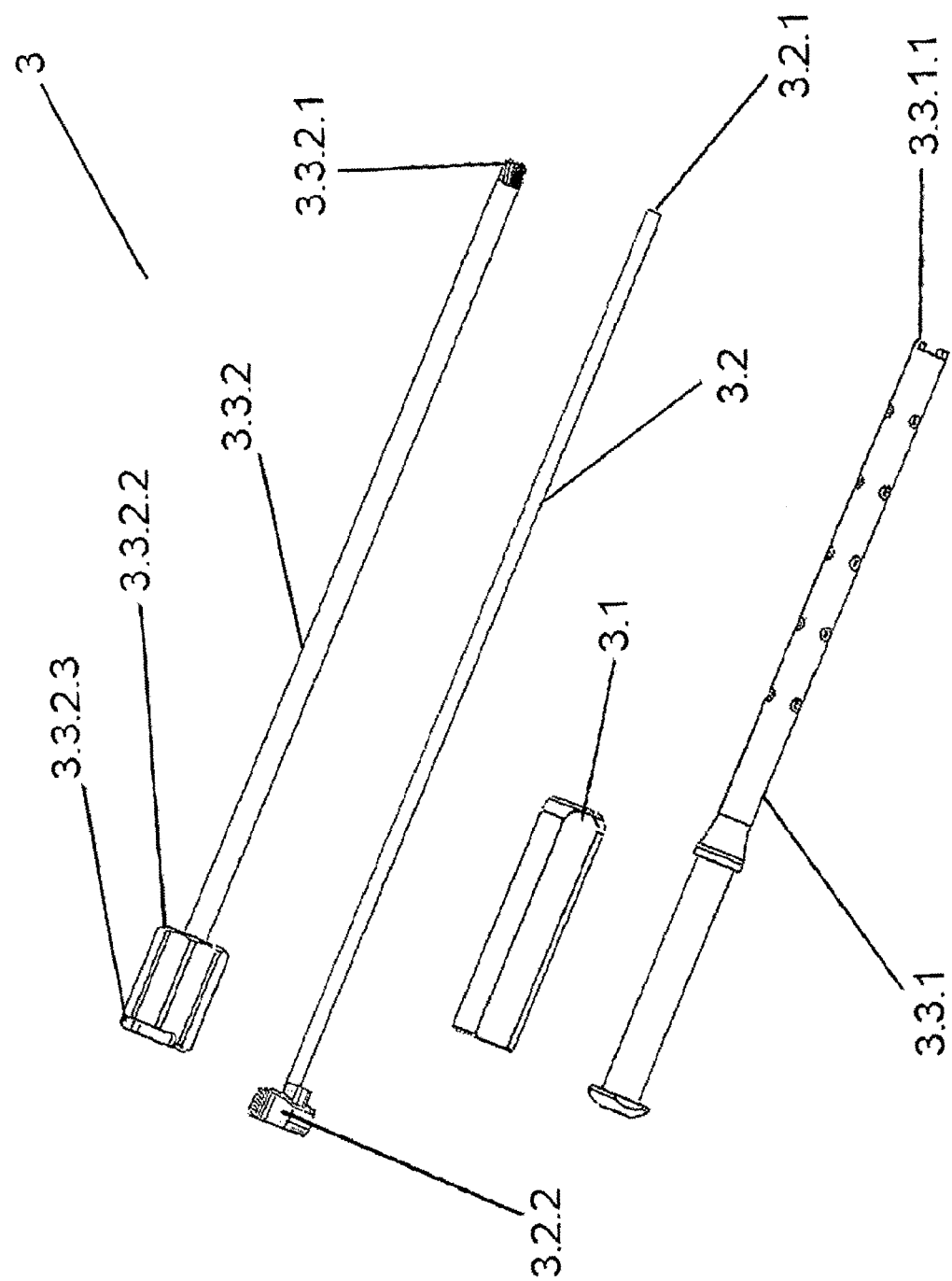

The instrument (3) shown in detail in FIGS. 4 and 5, comprises a handle (3.1) which enables firm grip of the instrument (3), cage fixator (3.3) and shaft adapter (3.2). Furthermore, cage fixator comprises an outer cage fixator (3.3.1) and an inner cage fixator (3.3.2). There are cage fixator claws (3.3.1.1) at the tip of the outer cage fixator (3.3.1). The inner cage fixator (3.3.2) comprises cage fixator threads (3.3.2.1) at its tip and an inner cage turning fixator (3.3.2.2) and a shaft adapter handle stopper (3.3.2.3).

As an advantage, the cage fixator claws (3.3.1.1) which are at the tip of outer cage fixator (3.3.1), are designed to sit into instrument hollow (1.5) at the back of the cage (1). When the cage fixator claws (3.3.1.1) is fixed into instrument hollow (1.5), with the help of lower and upper tabs located at the back of the cage (1) which outlines the lower and upper frame of the hollow (1.5), the rotating movement of outer cage fixator (3.3.1) is prevented and the first step of the fixation is achieved. Secondly, inner cage fixator (3.3.2) achieves the second fixation by turning the inner cage turning fixator (3.3.2.2) (this turning movement enables the cage fixator threads (3.3.2.1) to hold on to the threads in the threaded instrument hole (1.6) at the back of the cage (1)). With this fixation, sitting of the shaft adapter end (3.2.1) on the cornered back end (2.2) of the shaft (2) is also achieved. In this way, the instrument (3) fixes the expandable cage (1) by holding firmly on to the instrument hole (1.6) at the back of the expandable cage (1).

As an advantage, the shaft adapter end (3.2.1) is designed to fit firmly to the cornered back end (2.2) of the shaft (2). In this way, the shaft (2) can be fully and strongly turned and the expandable cage (1) is brought to expanded position.

As an advantage, the shaft adapter handle (3.2.2) at the back of the instrument (3) is designed such that it can be firmly grasped by the hand of the surgeon and can move only 90 degrees. The turning movement of the shaft adapter handle (3.2.2) is limited by the shaft adapter handle stopper (3.3.2.3) on the inner cage fixator (3.3.2). In this way, it is ensured that the shaft (2) cannot be turned more than 90 degrees in the expandable cage (1) and the irreversibility of the expansion property of the system is secured.

In a sample application of the invention;

The height between the vertebras in the operation area is measured and suitable size of the expandable cage (1) is determined. The suitably sized expandable cage (1) is locked to the instrument (3), with the help of threaded instrument hole (1.6) and instrument hollow (1.5) at the back of the expandable cage (1). During locking, the shaft adapter (3.2) is properly fitted to the cornered back end (2.2) of the shaft (2). Then the expandable cage (1) is implanted to its place between the two vertebras with the help of the instrument (3). After the expandable cage (1) is implanted, with the help of shaft adapter handle (3.2.2) of the instrument (3), the frontal expansion end (2.1) of the shaft (2) is turned 90 degrees, simultaneously sliding from outer socket (1.7.1) to the inner socket (1.7.2) at the front part of the expandable cage (1); then the expansion is achieved. In this way, the expansion is achieved by moving the expandable cage upper arm (1.1) and expandable cage lower arm (1.2) of the expandable cage (1) in opposite directions and the lower and upper teeth (1.4) fit completely into the vertebras. After controlling the position and the angle of the expandable cage (1) preferably with various imaging methods and being ensured of the proper position, the instrument (3) can be released from the cage (1) by turning the inner cage turning fixator (3.3.2.2) in the opposite direction. After that if requested, the bone graft can be injected into the shaft (2) with the help of graft filling hole (2.5) at the back of the shaft (2) and by using a proper apparatus. The filled in graft will flow through the graft holes (2.4) on the shaft (2) and fills the central space (1.8) within the cage (1), thus speeding up the fusion is ensured.

The invention is described by way of example above. Of course, the invention cannot be limited with the above described applications and the person skilled in the art can implement various variants of the invention without going beyond the ambit of the patent.

The invention claimed is:

1. An expandable cage (1) system comprising:
   a vertically expandable front part,
   a back part,
   a lower surface,
   an upper surface,
   an open position,
   a closed position,
   a cage length measured from the back part to the front part,
   an upper arm (1.1) located at the front part,
   a lower arm (1.2) located at the front part,
   an expandable cage cut (1.3) located between the upper arm (1.1) and the lower arm (1.2),
   an outer socket (1.7.1) located inside the expandable cage cut (1.3),
   an inner socket (1.7.2) located inside the outer socket (1.7.1),
   lower and upper teeth (1.4) respectively located at the lower and the upper surfaces,
   an instrument hollow (1.5) located at the back part,
   a threaded instrument hole (1.6) located at the back part,
   a central space (1.8),
   a horizontal axis extending from the back part to the front part, and
   a shaft (2) extending from the back part to the front part, the shaft (2) being restricted to a single 90° rotation movement around the horizontal axis and having:
   a shaft length being substantially the same as the cage length;
   a frontal expansion end (2.1) placed at the front part in the outer socket (1.7.1);
   a cornered back end (2.2) placed at the back part; and
   a shaft body (2.3) located between the frontal expansion end (2.1) and the cornered back end (2.2), wherein
   a. at the closed position, the frontal expansion end (2.1) of the shaft (2) sits in the outer socket (1.7.1), b. during the 90° rotation movement of the shaft (2), the frontal expansion end (2.1) slides from the outer socket (1.7.1) into the inner socket (1.7.2), and c. after the 90° rotation movement of the shaft (2), the system irreversibly reaches the open position, the upper arm (1.1) and the lower arm (1.2) are further separated, and the frontal expansion end (2.1) is locked in the inner socket (1.7.2) to prevent accidental movement of the shaft (2).

2. An expandable cage (1) system according to claim 1, wherein the shaft (2) has no further rotational moving capability around the horizontal axis after the single 90° rotation movement configured for the system to irreversibly transit from the closed position to the open position.

3. An expandable cage (1) system according to claim 1, wherein a. the back end (2.2) and the shaft body (2.3) are hollow, b. the shaft body (2.3) further comprises at least one hole (2.4), and c. the back end (2.2) further comprises a graft filling hole (2.5) configured for a bone graft to be injected into the shaft (2) after the system is inserted between vertebras.

4. An expandable cage (1) system according to claim 1, wherein the back end (2.2) of the shaft (2) is square or hexagonal or octagonal and the frontal expansion end (2.1) is rectangular prism-shaped.

5. An expandable cage (1) system according to claim 1, wherein a height of the inner socket (1.7.2) is greater than a height of the outer socket (1.7.1), and a width of the frontal expansion end (2.1) of the shaft (2) at the closed position is greater than a height of the frontal expansion end (2.1) and the height of the inner socket (1.7.2).

* * * * *